United States Patent
Sawa

(10) Patent No.: US 9,907,750 B2
(45) Date of Patent: Mar. 6, 2018

(54) TWO-LAYER SEPARATION-TYPE EYE DROP CONTAINING SQUALANE

(71) Applicant: SENJU PHARMACEUTICAL CO., LTD., Osaka-shi, Osaka (JP)

(72) Inventor: Shirou Sawa, Kobe (JP)

(73) Assignee: SENJU PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 14/778,359

(22) PCT Filed: Mar. 18, 2014

(86) PCT No.: PCT/JP2014/057211
§ 371 (c)(1),
(2) Date: Sep. 18, 2015

(87) PCT Pub. No.: WO2014/148450
PCT Pub. Date: Sep. 25, 2014

(65) Prior Publication Data
US 2016/0067181 A1    Mar. 10, 2016

(30) Foreign Application Priority Data

Mar. 19, 2013  (JP) ................. 2013-055929

(51) Int. Cl.
| | |
|---|---|
| *A61K 9/08* | (2006.01) |
| *A61K 47/32* | (2006.01) |
| *A61K 31/01* | (2006.01) |
| *A61K 31/728* | (2006.01) |
| *A61K 9/00* | (2006.01) |
| *A61K 47/26* | (2006.01) |

(52) U.S. Cl.
CPC .............. *A61K 9/08* (2013.01); *A61K 9/0048* (2013.01); *A61K 31/01* (2013.01); *A61K 31/728* (2013.01); *A61K 47/26* (2013.01); *A61K 47/32* (2013.01)

(58) Field of Classification Search
None
See application file for complete search history.

(56) References Cited

U.S. PATENT DOCUMENTS

| | | | |
|---|---|---|---|
| 2007/0265353 A1 | 11/2007 | Matsuhisa | |
| 2009/0196845 A1* | 8/2009 | Xia ................. | A01N 33/12 424/78.04 |

FOREIGN PATENT DOCUMENTS

| | | |
|---|---|---|
| EP | 1782801 A1 | 5/2007 |
| EP | 2070518 A2 | 6/2009 |
| JP | 10218760 A | 8/1998 |
| JP | 2007211008 A | 8/2007 |
| WO | WO-2006009101 A1 | 1/2006 |
| WO | WO-2006022291 A1 | 3/2006 |

OTHER PUBLICATIONS

International Search Report dated May 13, 2014 corresponding to International Application No. PCT/JP2014/057211.
European Search Report dated Aug. 11, 2016, corresponding to European Application No. EP14767461.

* cited by examiner

*Primary Examiner* — Shaojia A Jiang
*Assistant Examiner* — Dale R Miller
(74) *Attorney, Agent, or Firm* — Hogan Lovells US LLP

(57) ABSTRACT

The purpose of the present invention is to provide a technique for formulating a two-layer separation-type ophthalmic solution in which, during storage, an aqueous layer and an oil-containing layer containing squalane are separated from each other, wherein it is possible to homogeneously disperse the oil-containing layer in the aqueous layer while suppressing foaming by shaking the ophthalmic solution before administration, and the homogeneous dispersed state is maintained in a stable manner at least until administration. A two-layer separation-type ophthalmic solution containing squalane and water, wherein hyaluronic acid and/or a salt thereof and polyvinyl alcohol are contained in the ophthalmic solution and the polyvinyl alcohol content is set to 0.025 to 0.1 w/v %, whereby it is possible to homogeneously disperse the oil-containing layer in the aqueous layer while suppressing foaming by shaking the ophthalmic solution before administration, and to maintain the homogeneous dispersed state in a stable manner at least until administration.

8 Claims, No Drawings

TWO-LAYER SEPARATION-TYPE EYE DROP CONTAINING SQUALANE

This application is a U.S. National Phase under 35 U.S.C. § 371 of International Application PCT/JP2014/057211, filed on Mar. 18, 2014, which claims priority to Japanese Patent Application No. 2013-055929 filed on Mar. 19, 2013. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to two-layer separation-type ophthalmic solution containing squalane. More specifically, the present invention relates to a two-layer separation-type ophthalmic solution in which, during storage, an aqueous layer and an oil-containing layer containing squalane are separated from each other, wherein the oil-containing layer can be homogeneously dispersed in the aqueous layer by shaking the ophthalmic solution before administration while foaming is suppressed, and the homogeneous dispersion can be stably maintained at least until administration.

BACKGROUND ART

In the modern society, stresses that affect the cornea and conjunctiva increase, such as wearing contact lens, technostress, contact with allergies, air pollution, which associates with increasing patients suffering from dry eye. Patients suffering from dry eye tend to have lower corneal and conjunctival functions than normal to easily cause corneal epithelial disorder, corneal epithelial erosion, corneal ulcer, conjunctivitis, keratitis, eye infections, or the like.

Conventionally known methods for the prophylaxis or treatment of dry eye or eye diseases associated with reduced corneal and conjunctival functions include protecting the cornea and conjunctiva through administration of ophthalmic solution containing viscoelastic substances, such as chondroitin sulfate and hyaluronic acid, to impart water retention. The ophthalmic solution containing viscoelastic substances, however, may fail to provide a sufficient therapeutic effect because of insufficient protection for the cornea or conjunctiva. Therefore, there is a need for developing novel ophthalmic solution.

Ophthalmic solutions containing squalane have been recently reported to be effective for eye diseases such as dry eye. For example, the following ophthalmic solutions have been reported: an ophthalmic solution containing squalane is effective for the treatment of dry eye because it has an action to inhibit water evaporation (see Patent Document 1); an ophthalmic solution containing an oil, such as squalane, and a mucopolysaccharide is effective for the prophylaxis or improvement of dry eye associated with enhanced evaporation of tear fluid (see Patent Document 2); an ophthalmic solution containing squalane and vitamin E is effective for the treatment of inflammatory eye diseases (see Patent Document 3); and the like.

Since squalane thus has an activity to protect the cornea and the conjunctiva, the ophthalmic solution containing squalane are considered effective for the prophylaxis or treatment of dry eye as well as eye diseases associated with reduced corneal and conjunctival functions. Thus practical application of the ophthalmic solution containing squalane has been desired. Since squalane is oil and thus not compatible with water, ophthalmic solution containing squalane are typically designed as non-aqueous formulations, ophthalmic ointments, or emulsion formulations. Non-aqueous formulations and ophthalmic ointments, however, disadvantageously tend to cause pain at administration, blurred vision, stickiness, or others, which hinders continued use. Emulsion formulations containing squalane disadvantageously involve addition of a significant amount of surfactants to emulsify squalane, which causes irritations at administration or induces side effects. Furthermore, emulsion formulations containing squalane also disadvantageously require a large emulsifying device to be homogeneous an oil layer containing squalane in an aqueous layer in industrial manufacturing.

Patent Document 1 has reported a two-layer separation-type ophthalmic solution including two separate layers of an oil layer containing squalane and an aqueous layer, wherein the oil layer can be dispersed in the aqueous layer by shaking the ophthalmic solution before administration. Such a two-layer separation-type ophthalmic solution advantageously causes no reduction in comfort during use, unlike non-aqueous formulations nor ophthalmic ointments, because of the fact that the oil layer containing squalane is dispersed in the aqueous layer in the use of the ophthalmic solution, and further eliminates the need for a large amount of surfactants added or a large emulsifying device in manufacturing, unlike emulsion formulations. The two-layer separation-type ophthalmic solution containing squalane, however, may suffer from foaming by shaking before administration or a difficulty in achieving homogeneous dispersion of the oil layer in the aqueous layer only by shaking. The two-layer separation-type ophthalmic solution containing squalane may cause separation of the oil layer and the aqueous layer immediately after the oil layer is temporarily dispersed in the aqueous layer by shaking before administration, resulting in uneven concentration distribution of active ingredients, such as squalane, in the ophthalmic solution at administration. The ophthalmic solution with foaming or uneven dispersion thus fails to achieve homogeneous concentration of active ingredients, such as squalane, throughout the ophthalmic solution to cause uneven doses of active ingredients, which may inhibit achievement of expected prophylactic or therapeutic effects. Such problems have not been overcome by conventional techniques to hinder practical application of two-layer separation-type ophthalmic solution containing squalane.

PRIOR ART DOCUMENTS

Patent Documents

Patent Document 1: Japanese Patent Laid-open Publication (JP-A) No. 10-218760
Patent Document 2: JP-A No. 2007-211008
Patent Document 3: WO 2006/22291

SUMMARY OF THE INVENTION

Problems to be Solved by the Invention

An object of the present invention is to provide a technique for formulating a two-layer separation-type ophthalmic solution in which, during storage, an aqueous layer and an oil-containing layer containing squalane are separated from each other, wherein the oil-containing layer can be homogeneously dispersed in the aqueous layer by shaking the ophthalmic solution before administration while foaming is suppressed, and the homogeneous dispersion is stably maintained at least until administration.

Means for Solving the Problem

The intensive studies of the present inventors to solve the above-described problems have found that a two-layer separation-type ophthalmic solution containing squalane and water is allowed to further contain hyaluronic acid and/or its salt and polyvinyl alcohol, wherein the content of polyvinyl alcohol is set to 0.025 to 0.1 w/v %, whereby the oil-containing layer can be homogeneously dispersed in the aqueous layer by shaking the ophthalmic solution before administration while foaming is suppressed, and the homogeneous dispersion is stably maintained at least until administration. Further studies based on such a finding have completed the present invention.

That is, the present invention provides a two-layer separation-type ophthalmic solution in the following aspects.

Item 1. A two-layer separation-type ophthalmic solution comprising an oil-containing layer and an aqueous layer, wherein
the oil-containing layer contains squalane,
the aqueous layer contains hyaluronic acid and/or its salt and polyvinyl alcohol, with 0.025 to 0.1 w/v % of polyvinyl alcohol being present in the ophthalmic solution.

Item 2. The two-layer separation-type ophthalmic solution according to Item 1, comprising 0.1 to 0.5 w/v % of hyaluronic acid and/or its salt.

Item 3. The two-layer separation-type ophthalmic solution according to Item 1 or 2, comprising 1 to 10 w/v % of squalane.

Item 4. The two-layer separation-type ophthalmic solution according to any one of Items 1 to 3 wherein the ophthalmic solution is for non-human mammals.

Item 5. The two-layer separation-type ophthalmic solution according to any one of Items 1 to 4, comprising 0.2 to 10 parts by weight of polyvinyl alcohol per 100 parts by weight of squalane.

Item 6. The two-layer separation-type ophthalmic solution according to any one of Items 1 to 5, wherein the ophthalmic solution is for treatment of dry eye.

Item 7. The two-layer separation-type ophthalmic solution according to any one of Items 1 to 5 wherein the ophthalmic solution is for protecting cornea.

Item 8. Use of the two-layer separation-type ophthalmic solution according to any one of Items 1 to 5 for the manufacture of an agent for treatment of dry eye.

Item 9. Use of the two-layer separation-type ophthalmic solution according to any one of Items 1 to 5 for the manufacture of an agent for protecting cornea.

Item 10. A method of treating dry eye, comprising a step of administering the two-layer separation-type ophthalmic solution according to Items 1 to 5 to mammalian eyes suffering from dry eye.

Item 11. A method of protecting the cornea, comprising a step of administering the two-layer separation-type ophthalmic solution according to Items 1 to 5 to mammalian eyes requiring corneal protection.

Advantages of the Invention

According to the two-layer separation-type ophthalmic solution of the present invention, the oil-containing layer containing squalane is separated from the aqueous layer during storage and the oil-containing layer can be homogeneously dispersed in the aqueous layer by shaking the ophthalmic solution before administration while foaming is suppressed. Furthermore, according to the two-layer separation-type ophthalmic solution of the present invention, the homogeneous dispersion of the oil-containing layer in the aqueous layer can be stably maintained by temporarily shaking the ophthalmic solution before administration, whereby the homogeneous dispersion of squalane can be maintained at least until administration. In addition, the two-layer separation-type ophthalmic solution of the present invention eliminates the need for the step of homogenizing the ophthalmic solution during the manufacture, resulting in simple manufacture. This can overcome drawbacks of non-aqueous formulations, ophthalmic ointments, and emulsion formulations.

Since the two-layer separation-type ophthalmic solution of the present invention has good effect of inhibiting water evaporation and provides good protection for the cornea and the conjunctiva, it is effective for the prophylaxis or treatment of dry eye as well as eye diseases associated with reduced corneal and conjunctival functions.

Embodiments of the Invention

The two-layer separation-type ophthalmic solution of the present invention is a two-layer separation-type ophthalmic solution including an oil-containing layer and an aqueous layer, wherein the oil-containing layer contains squalane, and the aqueous layer contains hyaluronic acid and/or its salt and polyvinyl alcohol, with 0.025 to 0.1 w/v % of polyvinyl alcohol being present in the ophthalmic solution. As used herein, the term "two-layer separation-type ophthalmic solution" refers to an ophthalmic solution in which, during storage, an oil-containing layer and an aqueous layer are separated from each other, wherein the oil-containing layer can be dispersed in the aqueous layer by shaking the ophthalmic solution before administration for use. The two-layer separation-type ophthalmic solution of the present invention is described below in more detail.

Ingredients

The two-layer separation-type ophthalmic solution of the present invention contains squalane. Squalane is an oil and fat referred to also as 2,6,10,15,19,23-hexamethyl tetracosane. Squalane used in the present invention may be either semisynthetic one obtained by reduction of naturally occurring squalene, or synthetic one obtained by chemical synthesis. Semisynthetic squalane can be obtained by reduction of squalene present in deep sea fish, such as sharks, or olive oil, rice bran oil, wheat germ oil, sesame oil, cotton seed oil, or the like. Synthetic squalane can be obtained by synthesis using geranylacetone and acetylene compounds as raw materials.

Although the content of squalane in the two-layer separation-type ophthalmic solution of the present invention is not limited to particular values and appropriately set according to the pharmacological action based on squalane, it is, for example, 1 to 10 w/v %, preferably 2 to 8 w/v %, more preferably 3 to 7 w/v % to further improve the effect of suppressing foaming and the dispersibility during shaking and the effect of maintaining the dispersion after shaking.

The two-layer separation-type ophthalmic solution of the present invention contains hyaluronic acid and/or its salt. Hyaluronic acid salts are any pharmaceutically acceptable salts, and examples thereof include alkali metal salts, such as sodium salt and potassium salt. In the present invention, hyaluronic acid and its salts may be used alone or may be used in combination. Of hyaluronic acid and its salts, hyaluronic acid salts are preferred, and sodium hyaluronate is more preferred.

Hyaluronic acid and/or its salts used in the present invention may be either natural product or synthetic one. For example, hyaluronic acid and/or its salts that can be used may be extracted from animal tissues, such as cockscombs, or may be produced by fermentation engineering using culture of microorganisms producing hyaluronic acid, such as *Streptococcus zooepidemicus*, or the like. The weight average molecular weight of hyaluronic acid and/or its salt is any value within the range that is generally employed in the ophthalmologic field, typically 500,000 to 1,200,000, preferably 600,000 to 1,200,000.

Although the content of hyaluronic acid and/or its salt in the two-layer separation-type ophthalmic solution of the present invention is not limited to particular values and appropriately set according to the pharmacological action based on hyaluronic acid and/or its salt, it is, for example, 0.1 to 0.5 w/v %, preferably 0.2 to 0.5 w/v %, more preferably 0.3 to 0.4 w/v % to further improve the effect of suppressing foaming and the dispersibility during shaking and the effect of maintaining the dispersion after shaking.

The two-layer separation-type ophthalmic solution of the present invention further contains polyvinyl alcohol. The viscosity of polyvinyl alcohol (4 w/w % solution) used in the present invention is any value within the range that is generally employed in the ophthalmologic field, typically 2 to 100 mm$^2$/s. As used therein, the term "viscosity of polyvinyl alcohol (4 w/w % solution)" refers to a value obtained by dissolving 4 w/w % of polyvinyl alcohol in purified water at 60° C. to 80° C., cooling the resulting solution, and measuring the viscosity of the solution at 20±0.1° C. with a capillary viscometer (The Japanese Pharmacopoeia 16th Edition, Viscosity Determination, Method I). Polyvinyl alcohol used in the present invention may be fully saponified or may be partially saponified.

In the two-layer separation-type ophthalmic solution of the present invention, the content of polyvinyl alcohol is set within the range of 0.025 to 0.1 w/v %. The two-layer separation-type ophthalmic solution containing squalane and water is thus allowed to further contain hyaluronic acid and/or its salt and a predetermined amount of polyvinyl alcohol, whereby the oil-containing layer containing squalane can be homogeneously dispersed in the aqueous layer while foaming due to the shaking of the ophthalmic solution before administration is suppressed, and the homogeneous dispersion can be stably maintained at least until administration. The content of polyvinyl alcohol in the two-layer separation-type ophthalmic solution of the present invention is preferably 0.025 to 0.05 w/v % to further improve the effect of suppressing foaming and the dispersibility during shaking and the effect of maintaining the dispersion after shaking.

The ratio of squalane and polyvinyl alcohol in the two-layer separation-type ophthalmic solution of the present invention is within the range that satisfies the above contents of squalane and polyvinyl alcohol. The content of polyvinyl alcohol is typically 0.2 to 10 parts by weight, preferably 0.3 to 5 parts by weight, more preferably 0.3 to 4 parts by weight per 100 parts by weight of squalane to further improve the effect of suppressing foaming and the dispersibility during shaking and the effect of maintaining the dispersion after shaking.

The two-layer separation-type ophthalmic solution of the present invention contains water as a base in addition to the above ingredients. In the two-layer separation-type ophthalmic solution of the present invention, water constitutes the balance other than the above ingredients and optionally added pharmacological ingredients and additives. The content of water is appropriately set according to the contents of other ingredients added. Specifically, the content of water in the two-layer separation-type ophthalmic solution of the present invention is, for example, 80 to 98 w/v %, preferably 90 to 97 w/v %, more preferably 93 to 96 w/v %.

The two-layer separation-type ophthalmic solution of the present invention may optionally contain other pharmacological ingredients in addition to the above-described ingredients. Examples of pharmacological ingredients that can be added include anti-inflammatory agents, such as glycyrrhizinate dipotassium, pranoprofen, allantoin, epsilon aminocaproic acid, bromfenac, ketorolac tromethamine, nepafenac, berberine chloride, berberine sulfate, sodium azulene sulfonate, zinc sulfate, zinc lactate, and lysozyme hydrochloride; antihistamines, such as chlorpheniramine maleate and diphenhydramine hydrochloride; antiallergic agents, such as sodium cromoglicate, ketotifen fumarate, acitazanolast, amlexanox, pemirolast potassium, and tranilast; antibiotics, such as norfloxacin, ofloxacin, lomefloxacin, levofloxacin, and gentamicin; vitamins, such as ascorbic acid, flavin adenine dinucleotide sodium, cyanocobalamine, pyridoxine hydrochloride, tocopherol acetate, retinol acetate, retinol palmitate, panthenol, calcium pantothenate, and sodium pantothenate; amino acids, such as aspartic acid, taurine, and sodium chondroitin sulfate; anticholinesterases, such as neostigmine methylsulfate; vasoconstrictors, such as naphazoline, tetrahydrozoline, epinephrine, ephedrine, phenylephrine, and dl-methylephedrine; therapeutic agents for keratoconjunctival (corneal and conjunctival) epithelial disorders, such as diquafosol sodium; sulfa drugs, such as sulfadiazine, sulfisoxazole, sulfisomidine, sulfadimethoxine, sulfamethoxypyridazine, sulfamethoxazole, sulfaethidole, sulfamethomidine, sulfaphenazole, sulfaguanidine, phthalylsulfathiazole, and succinylsulfathiazole. The compounds illustrated herein may be in the form of pharmaceutically acceptable salts or may be in the form of other salts. These pharmacological ingredients may be used alone or may be used in combination.

Furthermore, the two-layer separation-type ophthalmic solution of the present invention may optionally contain additives that are typically used in ophthalmic solution. Specific examples of such additives include buffers, isotonizing agents, solubilizing agents, viscous bases, chelating agents, cooling agents, pH adjusters, preservatives, stabilizers, and surfactants.

Examples of buffers include phosphate buffer, borate buffer, citrate buffer, tartrate buffer, acetate buffer, Tris buffer, and amino acids.

Examples of isotonizing agents include saccharides, such as sorbitol, glucose, and mannitol; polyhydric alcohols, such as glycerol and propylene glycol; salts, such as sodium chloride; and boric acid.

Examples of solubilizing agents include polyhydric alcohols, such as glycerol and macrogol.

Examples of viscous bases include water soluble polymers, such as polyvinylpyrrolidone, polyethylene glycol, and carboxy vinyl polymer; and celluloses, such as hydroxyethyl cellulose, methyl cellulose, hydroxypropyl cellulose, hydroxypropyl methylcellulose, and sodium carboxymethyl cellulose.

Examples of chelating agents include disodium edetate and citric acid.

Examples of cooling agents include 1-menthol, borneol, camphor, and eucalyptus oil.

Examples of pH adjusters include alkalis, such as sodium hydroxide and potassium hydroxide; and acids, such as acetic acid, citric acid, hydrochloric acid, phosphoric acid, and tartaric acid.

Examples of preservatives include sorbic acid, potassium sorbate, sodium benzoate, methyl parahydroxybenzoate, ethyl parahydroxybenzoate, propyl parahydroxybenzoate, chlorobutanol, chlorhexidine gluconate, boric acid, dehydroacetic acid, sodium dehydroacetate, benzethonium chloride, benzyl alcohol, zinc chloride, parachlorometaxylenol, chlorocresol, phenethyl alcohol, polidronium chloride, and thimerosal.

Examples of stabilizers include polyvinylpyrrolidone, sodium sulfite, monoethanolamine, glycerol, propylene glycol, cyclodextrin, dextran, ascorbic acid, disodium edetate, taurine, and tocopherol.

Examples of surfactants include nonionic surfactants, such as tyloxapol, polyoxyethylene hydrogenated castor oil, polyoxyethylene polyoxypropylene block copolymer, polyoxyethylene sorbitan fatty acid ester, and octoxynol; amphoteric surfactants, such as alkyl diaminoethylglycine and lauryldimethyl betaine aminoacetate; anionic surfactants, such as alkyl sulfate, N-acyl taurine salt, polyoxyethylene alkyl ether phosphate, and polyoxyethylene alkyl ether sulfate; cationic surfactants, such as alkyl pyridinium salts and alkylamine salts.

pH/Osmotic Pressure

The pH and osmotic pressure of the two-layer separation-type ophthalmic solution of the present invention are not limited to particular values as long as they are within the ranges acceptable for ophthalmic solution. Specifically, the pH of the two-layer separation-type ophthalmic solution of the present invention is about 3 to 9, preferably about 6.5 to 7.5. The osmotic pressure of the two-layer separation-type ophthalmic solution of the present invention is about 0.5 to 3, preferably about 0.9 to 1.1 as the ratio of osmotic pressure to physiological saline solution in accordance with the Japanese pharmacopoeia. The pH and the ratio of osmotic pressure here are the values measured while the oil-containing layer containing squalane is homogeneously dispersed in the aqueous layer.

Properties/Direction for Use

After the two-layer separation-type ophthalmic solution of the present invention is statically stored, the oil-containing layer and the aqueous layer are separated from each other. The oil-containing layer is the upper layer and the aqueous layer is the lower layer.

The oil-containing layer contains squalane and optionally added pharmacological ingredients and additives that are compatible with squalane. The oil-containing layer may be either in the form of an oil layer composed of squalane-containing oil or in the form of an emulsified layer in which squalane-containing oil is emulsified, according to the types and contents of pharmacological ingredients and additives that are added to the two-layer separation-type ophthalmic solution of the present invention.

The aqueous layer contains hyaluronic acid and/or its salt, polyvinyl alcohol, water, and optionally added pharmacological ingredients and additives that are compatible with water.

Shaking the two-layer separation-type ophthalmic solution of the present invention before administration causes the oil-containing layer to be homogeneously dispersed and emulsified in the aqueous layer as fine oil droplets. After the oil-containing layer is temporarily dispersed in the aqueous layer by shaking, the homogeneous dispersion is stably maintained typically for 30 seconds or more, preferably for 1 minute. The two-layer separation-type ophthalmic solution of the present invention thus can maintain the homogeneous dispersion at least for the time required for ordinary administration after the oil-containing layer is temporarily dispersed in the aqueous layer. This prevents separation of the oil-containing layer and the aqueous layer or uneven dispersion to avoid uneven doses of squalane or the like.

In order to homogeneously disperse the oil-containing layer in the aqueous layer in the two-layer separation-type ophthalmic solution of the present invention, an eye drop bottle containing the two-layer separation-type ophthalmic solution of the present invention is shaken by hand. More specifically, an eye drop bottle containing the two-layer separation-type ophthalmic solution of the present invention is shaken up and down about 5 to 20 reciprocating cycles.

After the two-layer separation-type ophthalmic solution of the present invention is temporarily brought by shaking into the state where the oil-containing layer is homogeneously dispersed in the aqueous layer, and then statically stored, the two-layer separation-type ophthalmic solution is returned to the state where the oil-containing layer is separated from the aqueous layer.

Production Method

The two-layer separation-type ophthalmic solution of the present invention can be produced in accordance with a preparation method known per se, for example, using the method described in General Rules for Preparations in the Japanese Pharmacopoeia 16th Edition. More specifically, the two-layer separation-type ophthalmic solution of the present invention can be produced by adding squalane, hyaluronic acid and/or its salt, polyvinyl alcohol, and optionally added pharmacological ingredients and additives, to water.

Applications

Since the two-layer separation-type ophthalmic solution of the present invention has a good action to inhibit water evaporation, it is useful for diseases associated with lipid abnormalities (reduced secretion, changes composition) in tear fluid, and can be thus used as therapeutic agents for dry eye, particularly therapeutic agents for evaporative dry eye. Since the two-layer separation-type ophthalmic solution of the present invention inhibits evaporation of tear fluid to protect the cornea, it can be used not only as therapeutic agents for dry eye but also as corneal protectants, for example, for the prophylaxis or treatment of keratoconjunctival (corneal and conjunctival) epithelial disorders, Sjogren's syndrome, Stevens-Johnson syndrome, blepharitis, conjunctivitis, scleritis, postoperative inflammation, pemphigoid, blepharitis marginalis, incomplete eyelid closure, and sensory nerve numbness.

The two-layer separation-type ophthalmic solution of the present invention can be also applied not only to human but also to non-human mammals, such as dogs, cats, hamsters, guinea pigs, ferrets, rabbits, and livestock.

In particular, the administration to non-human mammals has a specific problem that it takes a longer time than that to human. This is because human applies ophthalmic solution to eyes of non-human mammals while the non-human mammals are fixed so that they cannot move. On the other hand, the two-layer separation-type ophthalmic solution of the present invention can overcome such a problem at administration to non-human mammals since it can stably maintain the homogeneous dispersion of the oil-containing layer in the aqueous layer after shaking, which allows administration of the ophthalmic solution in an homogeneous dispersion even when the administration takes a longer time after shaking. In light of such advantageous effects of the present invention, suitable targets for application of the two-layer separation-type ophthalmic solution of the present invention are non-human mammals.

EXAMPLES

The present invention is described below in detail by way of Examples, but the present invention is not restricted by these.

Test Example 1

Evaluation on Condition of Foaming and Dispersibility

The ophthalmic solutions of Examples 1 to 6 and Comparative Examples 1 to 6 described in Table 1 were obtained according to an ordinary method. In Examples 1 to 6 and Comparative Examples 1 to 5, the ophthalmic solutions were apparently separated into two layers in the static state. The upper layer was an emulsion containing oil droplets and the lower layer was a transparent, colorless aqueous solution. In Comparative Example 6, the ophthalmic solution was a transparent, colorless aqueous solution.

A glass vial (4 mL volume, available from AS ONE Corporation) was filled with 3 mL of each ophthalmic solution obtained above and shaken vigorously 20 times. The appearance of each ophthalmic solution was observed for 1 minute after completion of shaking to evaluate the condition of foaming and the dispersibility. The condition of foaming and the dispersibility were evaluated by rating according to the following criteria.
<Criteria>
Condition of Foaming
  0: A large amount of foam was produced.
  1: A large amount of foam was produced but immediately reduced to an acceptable level.
  2: No foam was produced or only a little foam in an acceptable level for placing drops in the eye.

Dispersibility
  0: No emulsion occurred where oil floated to cause separation.
  1: Emulsion occurred but cloudy dispersion throughout the liquid was not maintained for 30 seconds or more.
  2: Emulsion occurred and cloudy dispersion throughout the liquid was maintained for 30 seconds or more.

The obtained results are shown in Table 1. The results indicated that the ophthalmic solutions containing squalane, sodium hyaluronate, polyvinyl alcohol, and water in the static state caused the separation of the aqueous layer and the oil-containing layer containing emulsified squalane. When the content of polyvinyl alcohol was from 0.025 to 0.1 w/v % in the ophthalmic solutions containing squalane, sodium hyaluronate, polyvinyl alcohol, and water, the ophthalmic solution achieved the homogeneous dispersion of fine oil droplets of squalane while suppressing foaming due to shaking, and furthermore maintained this homogeneous dispersion for 30 seconds or more (Examples 1 to 6). On the other hand, when the ophthalmic solution contained squalane, sodium hyaluronate, and water with no polyvinyl alcohol, shaking the ophthalmic solution even failed to provide dispersion of squalane-containing oil (Comparative Example 1). When the ophthalmic solution contained squalane, sodium hyaluronate, polyvinyl alcohol, and water, with the content of polyvinyl alcohol being more than 0.1 w/v %, shaking the ophthalmic solution provided relatively good dispersion of squalane-containing oil but caused significant foaming (Comparative Examples 2 to 4). Furthermore, when the ophthalmic solution contained squalane, polyvinyl alcohol, and water with no sodium hyaluronate, the ophthalmic solution suppressed foaming due to shaking to temporarily form a homogeneous dispersion, but failed to stably maintain the dispersion, and after 30 seconds, squalane-containing oil floated, resulting in the separation of the aqueous layer and the oil-containing layer containing emulsified squalane.

TABLE 1

| | | Example | | | | | | Comparative Example | | | | | |
|---|---|---|---|---|---|---|---|---|---|---|---|---|---|
| | | 1 | 2 | 3 | 4 | 5 | 6 | 1 | 2 | 3 | 4 | 5 | 6 |
| Sodium hyaluronate | | 0.3 | 0.3 | 0.3 | 0.4 | 0.3 | 0.3 | 0.3 | 0.3 | 0.3 | 0.3 | 0 | 0.3 |
| Squalane | | 5.0 | 5.0 | 5.0 | 5.0 | 3.0 | 7.0 | 5.0 | 5.0 | 5.0 | 5.0 | 5.0 | 0 |
| Polyvinyl alcohol[#1] | | 0.025 | 0.05 | 0.1 | 0.1 | 0.1 | 0.1 | 0 | 0.15 | 0.2 | 0.3 | 0.1 | 0.1 |
| Sodium dihydrogen phosphate dihydrate | | 0.2 | 0.2 | 0.2 | 0.2 | 0.2 | 0.2 | 0.2 | 0.2 | 0.2 | 0.2 | 0.2 | 0.2 |
| Sodium chloride | | 0.8 | 0.8 | 0.8 | 0.8 | 0.8 | 0.8 | 0.8 | 0.8 | 0.8 | 0.8 | 0.8 | 0.8 |
| Sodium hydroxide | | Appropriate amount | Appropriate amount | Appropriate amount | Appropriate amount | Appropriate amount | Appropriate amount | Appropriate amount | Appropriate amount | Appropriate amount | Appropriate amount | Appropriate amount | Appropriate amount |
| Purified water | | Balance | Balance | Balance | Balance | Balance | Balance | Balance | Balance | Balance | Balance | Balance | Balance |
| pH | | 7.0 | 7.0 | 7.0 | 7.0 | 7.0 | 7.0 | 7.0 | 7.0 | 7.0 | 7.0 | 7.0 | 7.0 |
| Total volume (mL) | | 100 | 100 | 100 | 100 | 100 | 100 | 100 | 100 | 100 | 100 | 100 | 100 |
| Evaluation results | Condition of foaming | 2 | 2 | 2 | 2 | 2 | 2 | 2 | 0 | 0 | 0 | 0 | 2 |
| | Dispersibility | 2 | 2 | 2 | 2 | 2 | 2 | 0 | 2 | 2 | 2 | 1 | — |
| | Total [#2] | 4 | 4 | 4 | 4 | 4 | 4 | 2 | 2 | 2 | 2 | 1 | — |

The unit of the content of each ingredient is w/v % in Table.
"—" means unmeasured or uncalculated in Table.
[#1] Polyvinyl alcohol used was the trade name "Gohsenol EG-05" (available from The Nippon Synthetic Chemical Industry Co., Ltd.).
[#2] The "total" means the total value of the rating for the condition of foaming and the rating for the dispersibility.

Test Example 2

Evaluation on Effect of Inhibiting Water Evaporation

The ophthalmic solutions of Examples 1 to 3 and Comparative Examples 1 to 6 prepared in Test Example 1 were evaluated for their effect of inhibiting water evaporation. Specifically, 3 ml of each ophthalmic solution in a glass vial (4 mL volume, available from AS ONE Corporation) was shaken vigorously 20 times, placed in a petri dish (45 mm in diameter, 17 mm in height), and stored with no cover at 25° C. and a relative humidity of 40% for 5 hours. After 0.5 hours, the residual ophthalmic solution was weighed, and the water evaporation rate (mg/min) was calculated.

The obtained results are shown in Table 2. The results showed that the ophthalmic solution containing squalane, sodium hyaluronate, polyvinyl alcohol, and water, with the content of polyvinyl alcohol being from 0.025 to 0.1 w/v %, exhibited a significantly low water evaporation rate, which indicated that such ophthalmic solution prevented the ocular mucous membrane from being dried and thus provided good corneal protection.

TABLE 2

|  | Water evaporation rate (mg/min) |
| --- | --- |
| Example 1 | 0.98 |
| Example 2 | 1.64 |
| Example 3 | 1.29 |
| Comparative Example 1 | 3.16 |
| Comparative Example 2 | 2.98 |
| Comparative Example 3 | 4.33 |
| Comparative Example 4 | 5.31 |
| Comparative Example 5 | 3.03 |
| Comparative Example 6 | 4.80 |

Preparation Examples

Preparation Examples of the two-layer separation-type ophthalmic solution of the present invention are described below.

TABLE 3

|  | Preparation Example 1 | Preparation Example 2 | Preparation Example 3 | Preparation Example 4 |
| --- | --- | --- | --- | --- |
| Sodium hyaluronate | 0.3 | 0.1 | 0.4 | 0.4 |
| Squalane | 5.0 | 4.0 | 3.0 | 7.0 |
| Polyvinyl alcohol | 0.05 | 0.1 | 0.05 | 0.025 |
| Sodium dihydrogen phosphate dihydrate | 0.2 | 0.2 | 0.2 | 0 |
| Boric acid | 0 | — | — | 1.0 |
| Sodium chloride | 0.8 | 0.8 | 0.8 | 0.4 |
| Benzalkonium chloride | 0.005% | — | — | — |
| Chlorhexidine gluconate | — | 0.005% | — | — |
| Potassium sorbate | — | — | 0.1 | — |
| Sodium hydroxide | Appropriate amount | Appropriate amount | Appropriate amount | Appropriate amount |
| Hydrochloric acid | Appropriate amount | Appropriate amount | Appropriate amount | Appropriate amount |
| Purified water | Balance | Balance | Balance | Balance |
| pH | 7.0 | 7.0 | 5.0 | 8.0 |
| Total volume (mL) | 100 | 100 | 100 | 100 |

The unit of the content of each ingredient is w/v % in Table.

The invention claimed is:

1. A two-layer separation-type ophthalmic solution comprising an oil-containing layer and an aqueous layer, wherein
when statically stored, an upper layer consisting of the oil-containing layer and a lower layer consisting of the aqueous layer are formed, the oil-containing layer contains squalane,
the aqueous layer contains hyaluronic acid and/or its salt and polyvinyl alcohol, with 0.3 to 0.4 w/v % of hyaluronic acid and/or its salt and 0.025 to 0.1 w/v % of polyvinyl alcohol being present in the ophthalmic solution.

2. The two-layer separation-type ophthalmic solution according to claim 1, comprising 1 to 10 w/v % of squalane.

3. The two-layer separation-type ophthalmic solution according to claim 1 wherein the ophthalmic solution is for non-human mammals.

4. The two-layer separation-type ophthalmic solution according to claim 1, comprising 0.2 to 10 parts by weight of polyvinyl alcohol per 100 parts by weight of squalane.

5. The two-layer separation-type ophthalmic solution according to claim 1, wherein the ophthalmic solution is for treatment of dry eye.

6. The two-layer separation-type ophthalmic solution according to claim 1 wherein the ophthalmic solution is for protecting cornea.

7. A method of treating dry eye, comprising a step of administering the two-layer separation-type ophthalmic solution according to claim 1 to mammalian eyes suffering from dry eye.

8. A method of protecting the cornea, comprising a step of administering the two-layer separation-type ophthalmic solution according to claim 1 to mammalian eyes requiring corneal protection.

* * * * *